United States Patent
Myles

(10) Patent No.: US 8,385,502 B1
(45) Date of Patent: *Feb. 26, 2013

(54) TREATMENT PLANNING SIMULATION AND VERIFICATION SYSTEM

(75) Inventor: Jeremy R. Myles, West Sussex (GB)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/882,146

(22) Filed: Sep. 14, 2010

Related U.S. Application Data

(63) Continuation of application No. 12/135,939, filed on Jun. 9, 2008, now Pat. No. 7,831,017, which is a continuation of application No. 10/607,082, filed on Jun. 25, 2003, now Pat. No. 7,412,029.

(51) Int. Cl.
*A61N 5/10* (2006.01)

(52) U.S. Cl. .......................................................... 378/65

(58) Field of Classification Search ...................... 378/65
See application file for complete search history.

(56) References Cited

U.S. PATENT DOCUMENTS

| | | | |
|---|---|---|---|
| 3,133,227 A | 5/1964 | Brown et al. | |
| 3,144,552 A | 8/1964 | Schonberg et al. | |
| 3,193,717 A | 7/1965 | Nunan | |
| 3,466,439 A | 9/1969 | Setala | |
| 3,906,233 A * | 9/1975 | Vogel | 378/65 |
| 4,149,247 A | 4/1979 | Pavkovich et al. | |
| 4,149,248 A | 4/1979 | Pavkovich et al. | |
| 4,208,675 A | 6/1980 | Bajon et al. | |
| 4,209,706 A | 6/1980 | Nunan | |
| 4,521,808 A | 6/1985 | Ong et al. | |
| 4,593,967 A | 6/1986 | Haugen | |
| 4,675,731 A | 6/1987 | Takasu et al. | |
| 4,679,076 A | 7/1987 | Vikterlöf et al. | |
| 4,726,046 A | 2/1988 | Nunan | |
| 4,741,621 A | 5/1988 | Taft et al. | |
| 4,825,393 A | 4/1989 | Nishiya | |
| 4,853,777 A | 8/1989 | Hupp | |
| 4,868,844 A | 9/1989 | Nunan | |
| 4,995,068 A | 2/1991 | Chou et al. | |
| 5,027,818 A | 7/1991 | Bova et al. | |
| 5,046,003 A | 9/1991 | Crawford | |
| 5,080,100 A | 1/1992 | Trotel | |
| 5,099,505 A | 3/1992 | Seppi et al. | |
| 5,117,445 A | 5/1992 | Seppi et al. | |
| 5,117,829 A | 6/1992 | Miller et al. | |

(Continued)

FOREIGN PATENT DOCUMENTS

| | | |
|---|---|---|
| DE | 4223488 | 1/1994 |
| DE | 19614643 | 10/1997 |

(Continued)

OTHER PUBLICATIONS

Andrew et al., "A Video-Based Patient Contour Acquisition System for the Design of Radiotherapy Compensators," Med Phys., 1989, 1 page.

(Continued)

*Primary Examiner* — Glen Kao
(74) *Attorney, Agent, or Firm* — Blakely, Sokoloff, Taylor & Zafman LLP

(57) ABSTRACT

A treatment planning, simulation, and verification system is described. According to one embodiment, a treatment plan and a fluoroscopy data image of a treatment volume are received and the treatment plan is automatically adjusted based on the movement of the fluoroscopy data image. According another embodiment, a system includes a treatment planning component to generate a treatment plan and a simulation component to simulate the execution of the treatment plan.

12 Claims, 5 Drawing Sheets

U.S. PATENT DOCUMENTS

| | | | |
|---|---|---|---|
| 5,138,647 | A | 8/1992 | Nguyen et al. |
| 5,168,532 | A | 12/1992 | Seppi et al. |
| 5,335,255 | A | 8/1994 | Seppi et al. |
| 5,394,452 | A | 2/1995 | Swerdloff et al. |
| 5,438,991 | A | 8/1995 | Yu et al. |
| 5,471,516 | A | 11/1995 | Nunan |
| 5,537,452 | A | 7/1996 | Shepherd et al. |
| 5,651,043 | A * | 7/1997 | Tsuyuki et al. ............. 378/65 |
| 5,692,507 | A | 12/1997 | Seppi et al. |
| 5,751,781 | A | 5/1998 | Brown et al. |
| 5,764,723 | A | 6/1998 | Weinberger et al. |
| 5,901,199 | A | 5/1999 | Murphy et al. |
| 5,956,382 | A | 9/1999 | Wiener-Avnear et al. |
| 6,031,888 | A | 2/2000 | Ivan et al. |
| 6,041,097 | A | 3/2000 | Roos et al. |
| 6,104,778 | A | 8/2000 | Murad |
| 6,104,780 | A | 8/2000 | Hanover et al. |
| 6,144,875 | A | 11/2000 | Schweikard et al. |
| 6,219,403 | B1 * | 4/2001 | Nishihara ............. 378/65 |
| 6,222,901 | B1 | 4/2001 | Meulenbrugge et al. |
| 6,301,325 | B1 | 10/2001 | Besson et al. |
| 6,307,914 | B1 | 10/2001 | Kunieda et al. |
| 6,325,537 | B1 | 12/2001 | Watanabe |
| 6,325,758 | B1 | 12/2001 | Carol et al. |
| 6,366,798 | B2 | 4/2002 | Green |
| 6,370,421 | B1 | 4/2002 | Williams et al. |
| 6,381,302 | B1 | 4/2002 | Berestov |
| 6,385,286 | B1 | 5/2002 | Fitchard et al. |
| 6,400,796 | B1 | 6/2002 | Munro et al. |
| 6,429,578 | B1 | 8/2002 | Danielsson et al. |
| 6,507,026 | B2 | 1/2003 | Sugawara et al. |
| 6,508,586 | B2 | 1/2003 | Oota |
| 6,516,046 | B1 | 2/2003 | Frohlich et al. |
| 6,535,574 | B1 | 3/2003 | Collins et al. |
| 6,549,802 | B2 | 4/2003 | Thornton |
| 6,661,870 | B2 | 12/2003 | Kapatoes et al. |
| 6,783,275 | B2 | 8/2004 | Ghelmansaral |
| 6,842,502 | B2 | 1/2005 | Jaffray et al. |
| 6,865,254 | B2 | 3/2005 | Nafstadius |
| 6,914,959 | B2 | 7/2005 | Bailey et al. |
| 7,831,017 | B2 * | 11/2010 | Myles ............. 378/65 |
| 2001/0001807 | A1 | 5/2001 | Green |
| 2001/0008271 | A1 | 7/2001 | Ikeda et al. |
| 2002/0193677 | A1 | 12/2002 | Thornton |
| 2003/0007601 | A1 * | 1/2003 | Jaffray et al. ............. 378/65 |
| 2003/0048868 | A1 | 3/2003 | Bailey et al. |
| 2004/0005027 | A1 | 1/2004 | Nafstadius |

FOREIGN PATENT DOCUMENTS

| | | |
|---|---|---|
| EP | 0062941 | 9/1984 |
| EP | 0205720 | 12/1986 |
| EP | 0480035 | 11/1994 |
| FR | 2269745 | 11/1975 |
| FR | 2551664 | 3/1985 |
| GB | 1328033 | 8/1973 |
| JP | HEI 5(1993)-57028 | 3/1993 |
| WO | WO 85/03212 | 8/1985 |

OTHER PUBLICATIONS

Balter, James M. et al., "Daily Targeting of Intrahepatic Tumors for Radiotherapy," Int. J. Radiation Oncology Biol. Phys., vol. 52, No. 1 (2002), pp. 266-271.

Bova, "Dosimetric Technique for Stereotactic Radiosurgery," 1990014129-WO-A1, 1990, 1 page.

Brewsterfuauf, "Automatic Generation of Beam Apertures," Medical Physics, 1993, 1 page.

Cho, Paul S. et al., "Cone-Beam CT for Radiotherapy Applications," Phys. Med. Biol., vol. 40 (1995), pp. 1863-1883.

Drake, D.G. et al, "Characterization of a Fluoroscopic Imaging System for kV and MV Radiography," Med. Phys., vol. 27, No. 5, May 2000, pp. 898-905.

Elliott, "Interactive Image Segmentation for Radiation Treatment Planning," IBM Systems Journal, 1992, Citation from Medline (R) Database, 1 page.

Fahrig, R. and Holdsworth, D. W., "Three-Dimensional Computed Tomographic Reconstruction Using a C-Arm Mounted XRII: Image Based Correction of Gantry Motion Nonidealities," Med. Phys., vol. 27, No. 1, Jan. 2000, pp. 30-38.

Felokamp, LA et al. "Practical Cone-Beam Algorithm," J. Opt. Soc. Am. A., vol. 1, No. 6, Jun. 1984; pp. 612-619.

Gademann et al., "Three-Dimensional Radiation Planning Studies on Clinical Integration," Strahlenther Onkol, 1993, 1 page.

Groh, B.A. et al., "A Performance Comparison of Flat-Panel Imager-Based MV and kV Conebeam CT," Med. Phys., vol. 29, No. 6, Jun. 2002, pp. 967-975.

Hara et al., "Radiotherapeutic System," 00480035-EP-B1, Citation from World Patent, 1994, 1 page.

Inamura, "CT Simulator for Radiotherapy," 63294839 JP, 1988, 1 page.

Jaffray, "Cone-Beam CT: Application in Image Guided External Beam-Radiotherapy and Brachtherapy," IEEE, 2000, 2 pages.

Jaffray, David A., Ph.D. et al., "A Radiographic and Tomographic Imaging System Integrated Into a Medical Linear Accelerator for Localization of Bone and Soft-Tissue Targets," Int. J. Radiation Oncology Biol. Phys., vol. 45, No. 3 (1999), pp. 773-789.

Jaffray, O.A. and Siewerdsen, J.H., "Cone-Beam Computed Tomography with a Flat Panel Imager. Initial Performance Characterization," Med. Phys., vol. 27, No. 6, Jun. 2000, 1311-1323.

Kazufumi, "Radiation Treatment Device," 05057028 JP, 1993, 1 page.

Keys, A CCTV-Microcomputer Biostereometric System for Use in Radiation Therapy (Topography, Medical Physics, Tissue Compensators), 1984, Citation from Energy Science and Technology, 1 page.

Kuhn, "AIM Project A2003: Computer Vision in Radiology (COVIRA)," Computer Methods and Programs in Biomedicine, 1994, Citation from Dissertation Abstracts, 1 page.

Kushima et al., "New Development of Integrated CT Simulation System for Radiation Therapy Planning," Kobs J Med Sci., 1993, Citation from Medline (R) Database, 1 page.

Kutcher et al., "Three dimensional radiation treatment planning," Citation from Engineering Index, 1988, 2 pages.

Masahiro et al., "Patient Beam Positioning System Using CT Images," Phys. Med. Biol., 1982, vol. 27, No. 2, pp. 301-305, printed in Great Britain.

MDS Nordion, "Advanced Workstation for Irregular Field Simulation and Image Matching," Copyright 1999, MDS Nordion, 7 pages.

Midgley, S. et al., "A Feasibility Study for Megavoltage Cone Beam CT Using a Commercial EPID," Phys. Med. Biol., vol. 43 (1998), pp. 155-169.

Mohan, "Intersection of Shaped Radiation Beams with Arbitrary Image Sections," Computer Methods Programs Biomed, 1987, 1 page.

Moore, "Radiation Image Generating System and Method," 1992020202-WO-A1, 1992, 1 page.

Moore, "Radiation Image Generating System and Method," Citation from US Patent, Issued 1993, 2 pages.

Mori et al., "Development of Advanced Multislice CT Scanner Aquilion," e-Medical Review, Toshiba Medical Systems Corporation, Nov. 2001, pp. 1-9.

Mosleh-Shirazi, Mohammad Amin et al., "A Cone-Beam Megavoltage CT Scanner for Treatment Verification in Conformal Radiotherapy," Radiotherapy and Oncology, vol. 48 (1998), pp. 319-328.

Nakagawa, Keiichi, M.D. et al., "Megavoltage CT-Assisted Stereotactic Radiosurgery for Thoracic Tumors: Original Research in the Treatment of Thoracic Neoplasms" In. J. Radiation Oncology Biol. Phys., vol. 48, No. 2, (2000), pp. 449-457.

Ning et al., "An Image Intensifier-Based Volume Tomographic Angiography Imaging System: System Evaluation," SPIE, vol. 2432, pp. 280-290, (1995).

Nishihara, "Therapeutic Apparatus," Issued 1991, 2 pages.

Pisani, Laura, M.S. et al., "Setup Error in Radiotherapy: On-line Correction Using Electronic Kilovoltage and Megavoltage Radiographs," int. J. Radiation Oncology Biol. Phys., vol. 47, No. 3 (2000), pp. 825-839.

Ragan, "Correction for Distortion in a Beam Outline Transfer Device in Radiotherapy CT Based Simulation," Med. Phys. 20 (1), Jan.-Feb. 1993, pp. 179-185.

Ragan, "Correction for Distortion in a Beam Outline Transfer Device in Radiotherapy CT-based Simulation," Med Phys., 1993, 1 page.

Redpath, et al., "Use of a Simulator and Treatment Planning Computer as a CT Scanner for Radiotherapy Planning," 1984, Citation from INSPEC., 1 page.

Reynolds, "An Algorithm for Three-Dimensional Visualization of Radiation Therapy Beams," Med Phys., 1988, 1 page.

Ruchala, K.J. et al., "Megavoltage CT on a Tomotherapy System," Phys. Med. Biol., vol. 44 (1999), pp. 2597-2621.

Seppi, "Computed Tomography Apparatus Using Image Intensifier Detector," 19920005671WO-A1, 1 page, (1992).

Siewerdsen, Jeffery H. and Jaffray, David A., "Cone-Beam Computed Tomography With a Flat-Panel Imager: Magnitude and Effects of X-Ray Scatter," Med. Phys., vol. 28, No. 2, Feb. 2001, pp. 220-231.

Siewerdsen, Jeffery H. and Jaffray, David A., "Optimization of X-Ray Imaging Geometry (With Specific Application to Flat-Panel Cone-Beam Computed Tomography)," Med. Phys., vol. 27, No. 8, Aug. 2000, pp. 1903-1914.

Swindell, William et al., "Computed Tomography with a Linear Accelerator with Radiotherapy Applications," Med. Phys., vol. 10, No. 4, Jul.-Aug. 1983; pp. 416-420.

Toshiba, Clinical Performance: Delivering upon the Promise of Multi-slice CT through Proven Performance, 2001, pp. 1-8.

Uematsu, Minoru et al., "Daily Positioning Accuracy of Frameless Stereotactic Radiation Therapy With a Fusion of Computed Tomography and Linear Accelerator (FOCAL) Unit: Evaluation of Z-Axis With a Z-Marker," Radiotherapy and Oncology, vol. 50, No. 3, Mar. 1999, pp. 337-339.

Uematsu, Minoru, M.D. et al. "Intrafractional Tumor Position Stability During Computed Tomography (CT)-Guided Frameless Stereotactic Radiation Therapy for Lung or Liver Cancers With a Fusion of CT and Linear Accelerator (FOCAL) Unit," Int. J. Radiation Oncology Biol. Phys., vol. 48, No. 2 (2000), pp. 443-448.

Uematsu, Minoru, M.D. et al., "A Dual Computed Tomography Linear Accelerator Unit for Stereotactic Radiation Therapy: A New Approach Without Cranially Fixated Stereotactic Frames," Int. J. Radiation Oncology Biol. Phys., vol. 35, No. 3 (1996), pp. 587-592.

\* cited by examiner

TREATMENT PLANNING SIMULATION AND VERIFICATION SYSTEM

This application is a continuation of U.S. patent application Ser. No. 12/135,939 filed Jun. 9, 2008 issued as U.S. Pat. No. 7,831,017 on Nov. 9, 2010 which is a continuation of U.S. patent application Ser. No. 10/607,082 filed Jun. 25, 2003 and issued as U.S. Pat. No. 7,412,019 on Aug. 12, 2008.

BACKGROUND OF THE INVENTION

1. Technical Field

Embodiments of the invention relate to the field of oncology systems and, more specifically, to a radiotherapy treatment simulation, planning, and verification system.

2. Background

An objective of radiation therapy is to maximize the amount of radiation to a target volume (e.g., a cancerous tumor) and minimize the amount of radiation to healthy tissues and critical structures. Verification of the location of the target volume prior to the administration of a dose of therapeutic radiation is key to the objective. Another objective is to minimize the amount of time to set up and administer the therapeutic radiation treatment. Typically, many clinics have to use linear accelerators for a considerable (e.g., 30-40 minutes) amount of time to start new patients with setup and treatment plan verification. Unfortunately, since care providers treat multiple patients and each patient is treated over 30 to 40 fractionated sessions, the time allowed for each session is relatively short, e.g. 10 to 15 minutes, so the process must be fast as well as accurate.

Radiotherapy simulator machines have traditionally been used to perform the pre-treatment analysis of the target volume before a radiotherapy treatment machine applies the therapeutic radiation. These radiotherapy simulators are a costly investment.

For example, among other components, a traditional radiotherapy simulator machine may use a bulky image intensifier tube detector and/or require time-consuming film processing to capture images of the target volume. Film processing includes questionable environmental, health, and safety issues. Furthermore, these image intensifier tube detectors have the disadvantage of being very large relative to their imaging area. They also have image spatial distortions from their spherical-shaped input surface and the orientation of the intensifier tube with the Earth's magnetic field.

One example of a simulator machine of the prior art is the Ximatron Simulator by Varian Medial Systems of Palo Alto, Calif. The Ximatron is limited by requiring treatment plans to be imported from another device (e.g., a CT scanner) for verification (e.g., verification of dose plans for irregular fields). Furthermore, if the treatment plan requires any adjustments based on the verification, the treatment plan must first be updated on the other device, and then the updated treatment plan must be imported back into the Ximatron for another verification. This prior art process would repeat if the verification requires further corrections. Therefore, this prior art process is very time-consuming and costly.

Another prior art device is the Helax simulator made by MDS Nordion. The Helax device provides for field shapes to be projected onto the skin of a patient for marking by means of a liquid-crystal display ("LCD") projection panel. The LCD panel is a separate component from the simulator and thus the LCD display must be fitted onto the outside of the head of the simulator. One problem with this arrangement is that the projected image is difficult to see. Furthermore, the LCD projection of the Helax simulator only projects one image onto a patient at a time.

SUMMARY OF AN EMBODIMENT OF THE INVENTION

A treatment planning, simulation, and verification system is described. According to one embodiment of the invention, a treatment plan and a fluoroscopy data image of a treatment volume are received, and the treatment plan is automatically adjusted based on the movement of the fluoroscopy data image.

According to one embodiment of the invention, a system includes a treatment planning component to generate a treatment plan and a simulation component to simulate the execution of the treatment plan.

According to one embodiment of the invention, a gantry includes a collimator and an LCD assembly integrated with the collimator to project one or more digital outlines onto a patient.

According to one embodiment of the invention, a digital fluoroscopic image of a target volume is provided. A catheter is placed near the target volume based on the fluoroscopic digital image and a radioactive isotope is placed within the catheter based on the digital fluoroscopic image.

According to one embodiment of the invention, a digital fluoroscopic image of a target volume is provided and a seed is placed near the target volume based on the fluoroscopic digital image.

According to one embodiment of the invention, a digital image of a patient is displayed based on a treatment plan, the digital image is corrected, and one or more components of a radiotherapy simulator system are automatically adjusted based on the corrected digital image.

It should be appreciated that the present invention may be implemented in numerous ways, including as a method, an apparatus, a system, or a machine-readable medium. Several inventive embodiments of the present invention are described below.

BRIEF DESCRIPTION OF THE DRAWINGS

The invention may best be understood by referring to the following description and accompanying drawings that are used to illustrate embodiments of the invention. In the drawings.

DETAILED DESCRIPTION

Figure 1A:
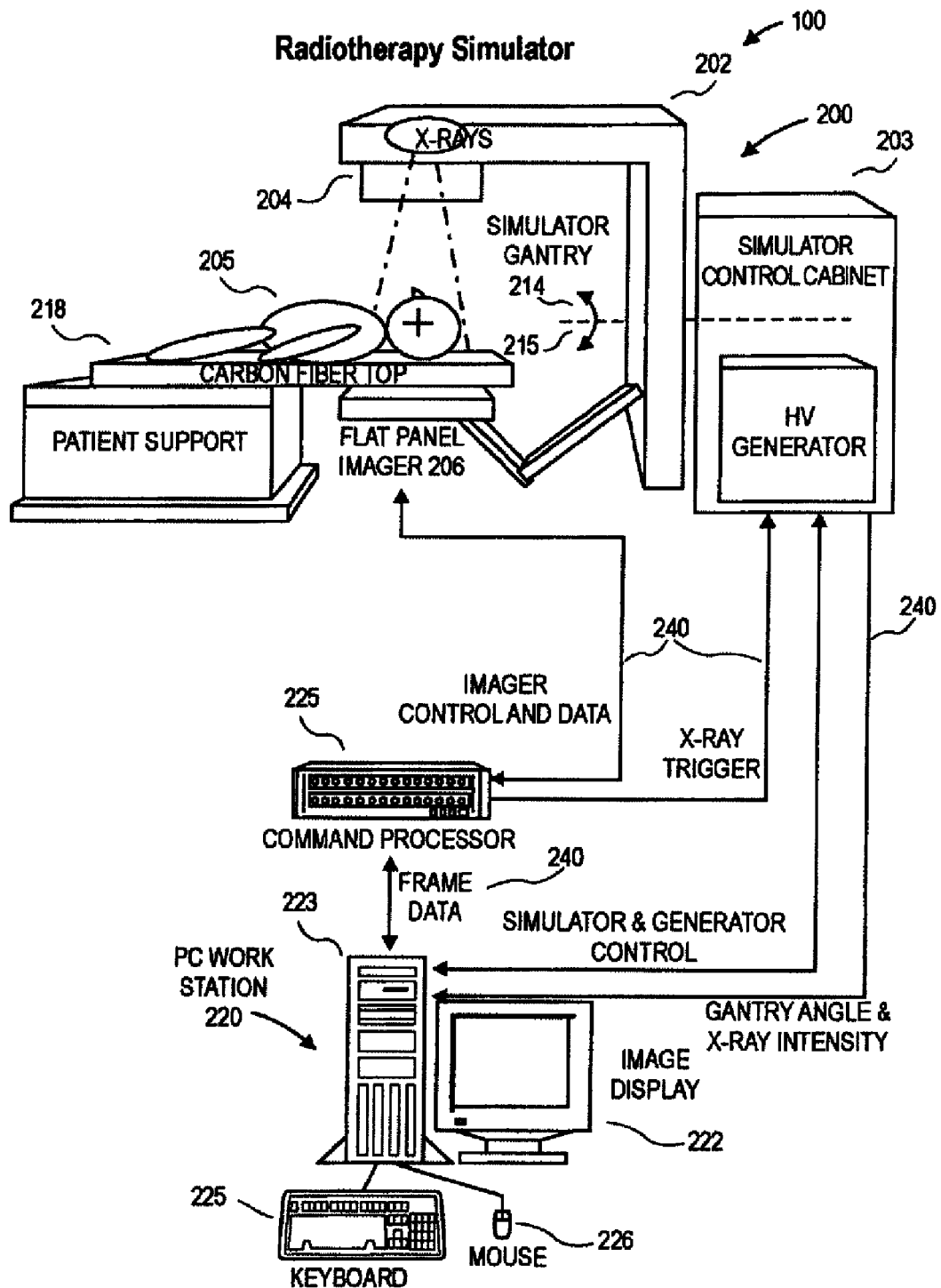
FIG. 1A is a side view of one embodiment of a simulation treatment system.

In the following description, for purposes of explanation, numerous specific details are set forth. It will be evident, however, to one skilled in the art that embodiments of the invention may be practiced without these specific details. In some instances, well-known structures, techniques and devices are not shown in detail in order to avoid obscuring the understanding of this description. These embodiments are described in sufficient detail to enable those skilled in the art to practice the invention, and it is to be understood that other embodiments may be utilized and that logical, mechanical, electrical and other changes may be made without departing from the scope of the present invention.

While the invention is described in conjunction with several embodiments, it should be understood that the invention is not limited to any one embodiment. On the contrary, the scope of the invention is limited only by the appended claims and the invention encompasses numerous alternatives, modifications, and equivalents. For the purpose of example, numerous specific details are set forth in the following description in order to provide a thorough understanding of the present invention. The present invention may be practiced according to the claims without some or all of these specific details. For the purpose of clarity, technical material that is known in the technical fields related to the invention has not been described in detail in order not to unnecessarily obscure the present invention.

A treatment planning, simulation, and verification system is described. Treatment simulation and verification are important steps in radiotherapy, particularly with the popularity of intensity modulated radiation therapy ("IMRT"). Clinicians begin the treatment process by acquiring detailed images of a patient's tumor and surrounding anatomy. These images are used within sophisticated treatment planning software to generate treatment plans that specify how a linear accelerator will deliver the prescribed radiation dose to tumors while minimizing the dose to surrounding healthy tissues during treatment. Since radiotherapy requires great precision, simulation, and verification processes are used to ensure that treatment plans will achieve the intended results. According to one embodiment of the invention, a treatment planning, simulation, and verification system provides for the integration of diagnostic and imported digitally reconstructed radiograph ("DRR") images from a computed tomography ("CT") scanner, which may be added to a patient's record immediately after capture. In this way, the treatment planning, simulation, and verification components of the system enable clinicians to fine-tune or update treatment plans by analyzing high-quality anatomical images of patients in their treatment positions. These images are used for comparisons with treatment plan reference images so that care providers may analyze and make necessary adjustments and corrections to the treatment plan immediately. This verification of the planned treatment can be carried out in a minimum amount of time because of the interactive nature of the integrated design with the computer planning software. The plans, after completion, can be immediately viewed in the system and the patient is set up automatically to these positions so that the target position and movement can be checked and monitored. Any changes needed may immediately be made and then the dose recalculated by the planning software. In an embodiment of the invention both the simulator control software and the planning software reside on the same system. Thus, allowing a physician to do image-guided radiotherapy using on-line verification of the patient's treatment position, as will be described.

In addition to verifying a treatment plan and minimizing the amount of time a patient spends in a treatment room during administration of the therapeutic radiation, the following will describe a manner in which the simulation need not include costly mechanical components included with traditional simulators, such as bulky image intensifiers and multileaf collimators ("MLC").

FIG. 1A is a side view of one embodiment of a simulation treatment system 100. As will be described, the simulation treatment system 100 includes hardware and software components to provide treatment planning, simulation, and verification. The simulation treatment system 100 includes a simulation machine 200, a treatment couch 218, a command processor module 225, a computer workstation 220 and a communications network 240. The simulation treatment machine 200 includes a rotatable gantry 202 pivotally attached to a drive stand 203. A gantry head 204 and a flat panel imager 206 oppose each other and are mechanically coupled to the rotatable gantry 202. In one embodiment, the gantry head 204 includes a collimator having an LCD assembly (not shown) and a radiation source (not shown).

Figure 1B:
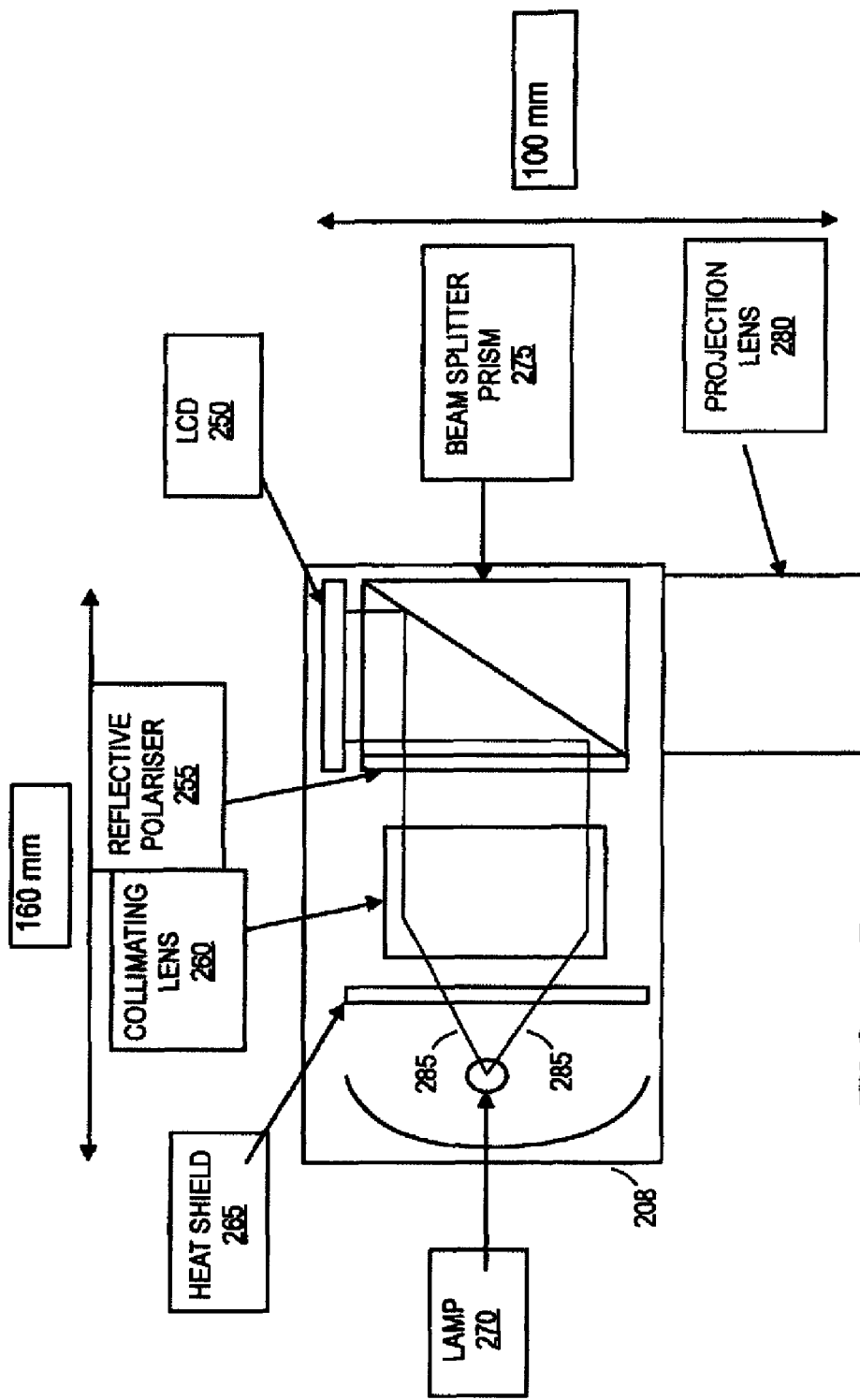
FIG. 1B illustrates one embodiment of an LCD assembly.

FIG. 1B illustrates one embodiment of the LCD assembly 208. The LCD assembly 208 includes an LCD 250, a reflective polariser 255, collimating lens 260, a heat shield 265, a lamp 270, a beam splitter prism 275, and a projection lens 280. In one embodiment, a light 285 from the lamp 270 projects through the heat shield 265, collimating lens 260, and reflective polariser 255 and reflects off the beam splitter prism 275 onto the LCD 250. The LCD 250 uses the light 285 to reflect a digital image (e.g., leaf position, a target volume, etc.) onto a patient. Since the LCD 208 assembly is integrated with the collimator, the LCD assembly 208 does not move and is more accurate. Therefore, it should be appreciated that unlike the current Helax system, the LCD 250 is not put onto the outside of the collimator every time it is needed for use. Rather, the LCD 250 is integrated into the collimator. This inherently helps to maintain the accuracy of the simulator treatment system 100. Furthermore, having the LCD 250 closer to the light 285 allows for a clearer image onto the patient.

Referring back to FIG. 1A, in one embodiment the flat-panel imager 206 may be an amorphous-silicon flat panel image detector that produces and displays high-resolution, distortion-free radiographic and fluoroscopic digital images on the computer workstation 220 via the communications network 240. The flat-panel imager 206 may include lag correction software to prevent distortion and ensure high resolution of the generated images, as will be described.

It should be appreciated that using the flat-panel imager 206 speeds the simulation and verification process by eliminating the need for time-consuming film processing and by providing increased flexibility in positioning patients as compared with traditionally used, bulky image intensifier tubes. Furthermore, the slimness of the flat-panel imager 206 greatly reduces the size of the detection system, as compared to an image intensifier enabling more treatment positions and allowing greater access to the patient for checking the setup. The flat-panel imager 206 is also fully retractable to increase the possible movement of an operator about the patient.

In one embodiment, the flat panel imager 206 is a real-time digital x-ray imager incorporating a large-area amorphous silicon sensor array with a high-sensitivity cesium iodide ("CsI") scintillator. The flat panel imager includes a receptor module that incorporates the amorphous silicon sensor array, which accepts incoming X-ray photons and converts them to a digital video signal. The receptor module may also include a power supply module (e.g., 24 VDC power), interconnecting cables (e.g., fiber optic control and data cables), and drive and readout circuits followed by digital data conversion and transmission capabilities well known to those of ordinary skill in the art.

It should be appreciated that the flat panel imager may be a two-dimensional, large flat panel imager that can operate, for example, at 15 to 30 frames per second ("fps") over a wide range of doses. In this way, fluoroscopic and digital radiographic imaging can all be achieved with the same flat panel system. By way of example, U.S. Pat. No. 5,970,115 entitled "Multiple Mode Digital X-Ray Imaging System," filed on Nov. 25, 1997, discloses a flat panel system that is hereby incorporated by reference in its entirety.

In one embodiment, the command processor module 225 manages the receptor module, processes the digital video signal, and provides interfaces to other components of the simulation treatment system 100. The command processor module 225 may include a microcontroller-based, single board computer running a real-time operating system with acquisition, control, and interface software. Also, included in the command processor module 225 may be a high-speed digital video interface card, a dedicated image processor card to perform real-time image corrections, a system interface card, and a parallel output to transmit image data to an external image processor and display. Scan-converted digital and analog video may also be provided.

The computer workstation 220 includes a computer 223, a display monitor 222, a keyboard 225, and a mouse 226. The computer 223 includes treatment planning, simulation, and verification software, as will be described. The display monitor 222 has the ability to display two-dimensional, three-dimensional, and four-dimensional information and images.

The treatment couch 218 is positioned adjacent to the gantry 202 to place the patient and the target volume within the range of operation for the gantry head 204 and the imager 206. The couch 218 may be connected to the rotatable gantry 202 via the communications network 240 and is capable of translating in multiple planes plus angulation for positioning and re-positioning the patient 205 and, therefore, the target volume.

The gantry 202 can rotate 214 about an isocenterline 215 to place the gantry head 204 and imager 206 at any position 360 degrees around the target volume, for example, to generate image data. In one embodiment, the isocenterline 215 is lower in height for ease of use (e.g., to allow easier access to the couch for the elderly and small persons). Also, increased isocentric accuracy needed for IMRT target definition is available because the radiation source is fixed into position.

Figure 2:
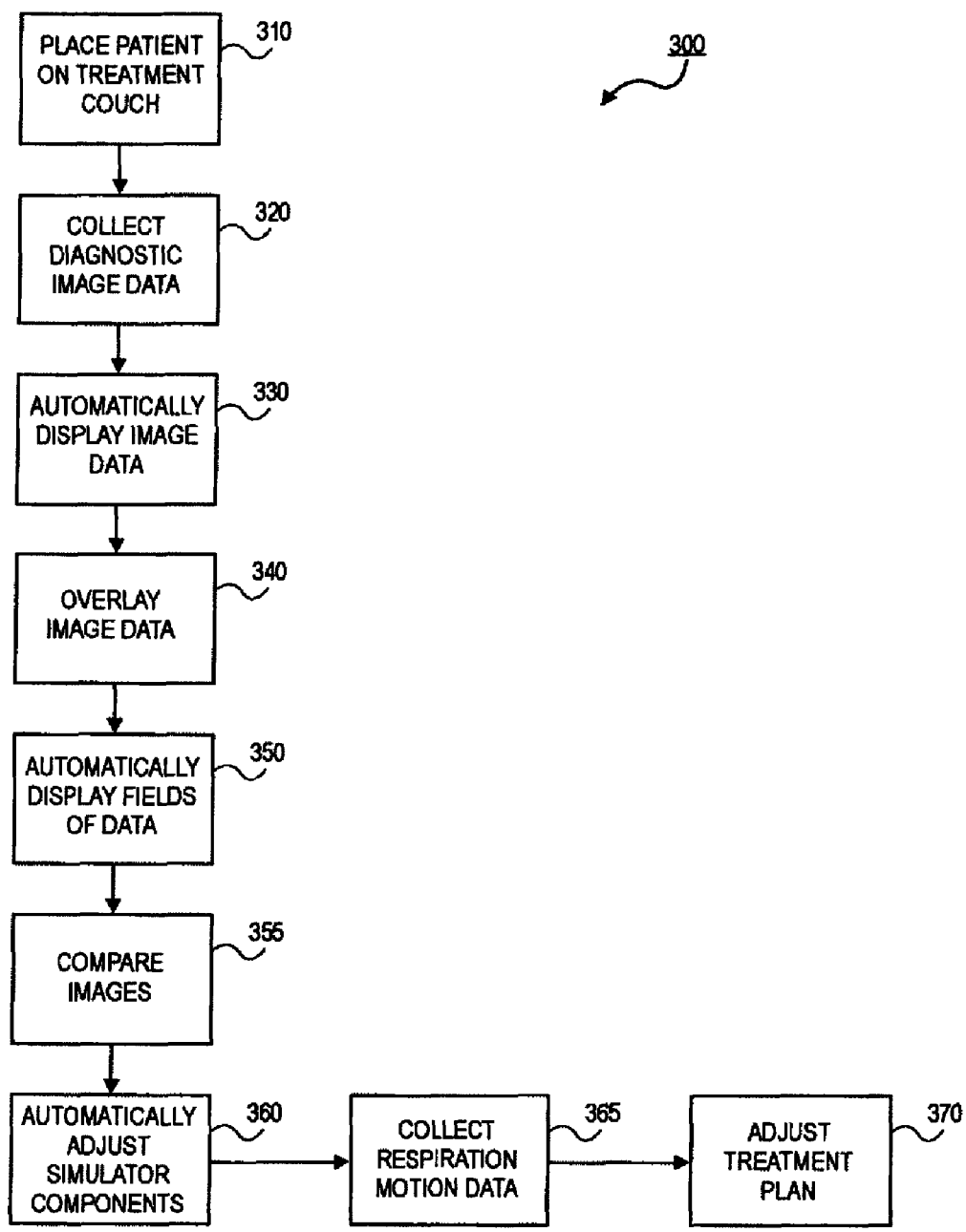
FIG. 2 illustrates one embodiment of a process to perform verification of a treatment position of a patient.

FIG. 2 illustrates one embodiment of a process (300) to perform verification of a treatment position of a patient. At step 310, a patient is placed on the treatment couch 218 and the couch 218 is positioned relative to the simulation device 200. At step 320, the gantry 202 can be positioned around the patient 205 while the radiation from the radiation source impinges the flat-panel imager 206. For example, the radiation source may be a high-resolution x-ray tube (e.g., a kilovoltage radiation source generally in the 50 to 150 kilovolt ("kV") energy range and, for example, at 125 kilovolts peak ("kVp")). The gantry 202 rotates and collects simulator image data and stores the data in the computer workstation 220. For example, the system 100 may produce fluoroscopic digital image(s) of the movement of the patient's internal anatomy.

The captured simulator image projection data may be delivered and stored to a computer 223. As shown in FIG. 1, the computer 223 connects to the simulator device 200 and the command processor 225 via communications network 240. The computer workstation 220 may control the synchronized movement of the simulator device 200, including the rotatable gantry 202, a radiation source, LCD assembly 208, flat panel imager 206 and the treatment couch 218. For example, an oncologist may use the workstation 220 to display image projection data on a display monitor 222, control the intensity of the radiation source, and control the gantry angle.

At step 330, the simulator digital image(s) of the target volume are displayed on the computer workstation 220. A treatment plan may be generated from the simulator device 200 or, for example, imported from a CT scanner that generated the DRR image of the target volume. At step 340, a DRR image and plan of the target volume is overlaid on the simulator digital image on the computer workstation display monitor 222.

At step 350, planned treatment fields are automatically displayed on the computer workstation display monitor 222. At step 355, a care provider may compare the previously planned positions with the overlaid images to determine any necessary corrections, such as by providing inputs associated with the overlaid images. For example, the care provider may check that the radiation fields are correct and that the set-up required can actually be mechanically achieved. Contouring may also be accomplished as necessary.

The largest field sizes may be viewed by digitally combining images. These combined images allow the care provider to view larger anatomical areas and facilitate the filmless radiotherapy department.

At step 360, components of the system 100 are automatically adjusted based on adjustments to the treatment plan positions on the workstation 220. All types of fields, including static and MLC fields, can be adjusted using image-controlled simulation. For example, the care provider may adjust the field position, field size and machine parameters directly by modifying the image at the workstation 220 by, for example, modifying (e.g., drag and drop) field wires, collimator rotation, and couch position on the specific image. In this way, the simulation machine 200 and/or the treatment couch 218 moves immediately to the new positions per the re-imaging. Furthermore, the treatment couch 218 may also be automatically adjusted for accurate patient positioning and immobilization.

At step 365, respiratory gating software, known in the art, on the computer workstation 220 (or on a separate system, not shown) collects respiration motion data, such as the patient's external breathing pattern and range of motion. A care provider may use the respiration motion data to compare and analyze how target volumes are displayed in the live, digital fluoro image, move as a patient breathes, and then adjust treatments to account for the motion. In this way, a care provider may modify plans by repositioning patients, changing treatment margins around the target volume, or planning the use of respiratory gating to administer radiation only during specified parts of the breathing cycle.

At step 370, any corrections to the treatment plan are automatically saved for plan recalculation and use by the therapeutic treatment machine.

It should be appreciated that in an alternative embodiment, the simulation machine 200 may generate a cone-beam CT scan of the target volume. This cone-beam CT scan may be used in place of or in addition to the previously disclosed importing. The computer workstation 220 may create a treatment plan based on the identified images, to be implemented by a therapeutic treatment device.

Figure 3:
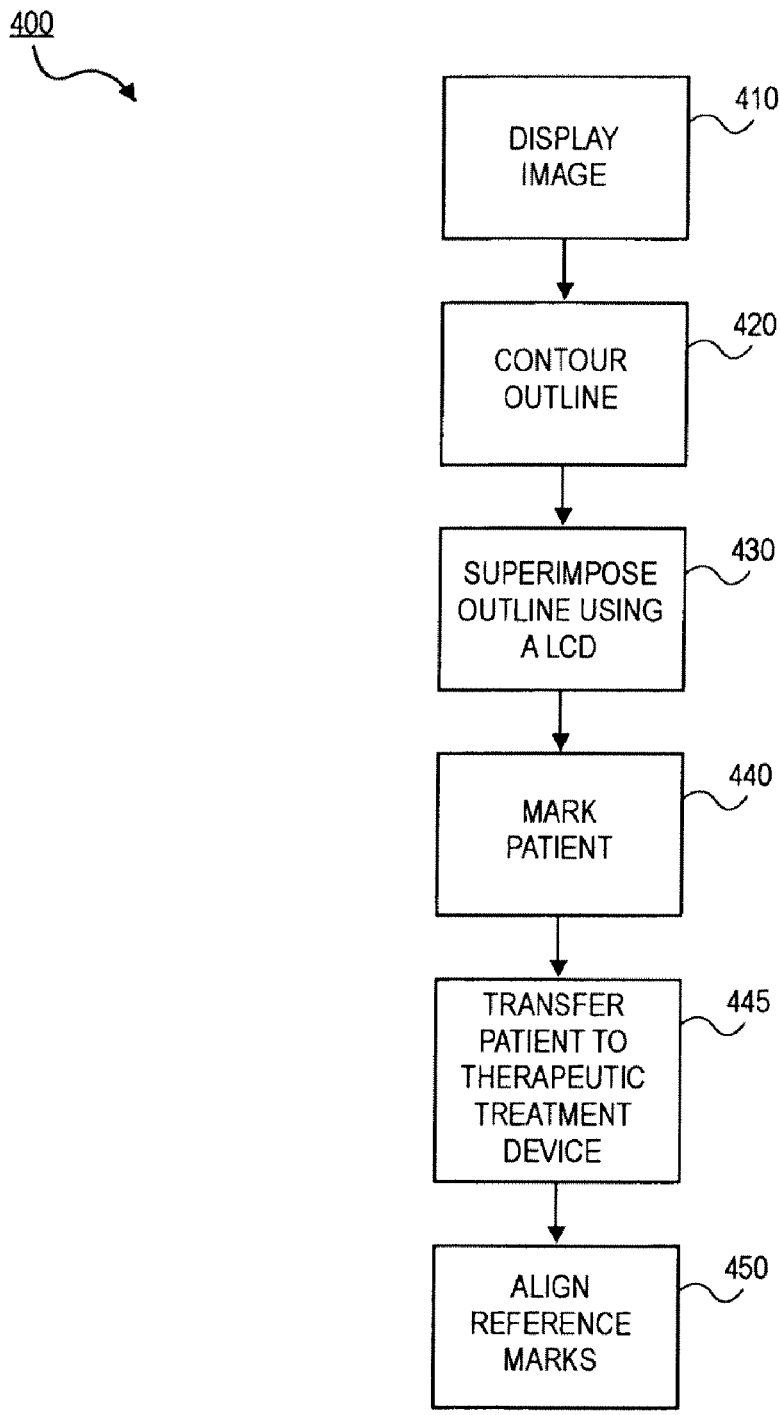
FIG. 3 illustrates one embodiment of a process to position a patient for radiotherapy.

Persistent and accurate positioning of a patient during therapeutic radiation treatment is desirable to prevent damaging healthy tissue. FIG. 3 illustrates one embodiment of a process (e.g. process 400) to position a patient for radiotherapy. At step 410, a digital image of a patient including a target volume is displayed on the computer workstation 220. At step 420, an outline of the treatment area is traced (e.g., contouring) on the digital image (e.g., two-dimensional image) of the patient on the display monitor 222. At step 430, the traced image of the outline is superimposed or projected onto the patient. For example, this allows for the viewing and verification of MLC leaf positions or other shielding devices defined in the treatment plan.

In one embodiment, the LCD assembly 208 may project a visual light beam of the outlines onto the patient, including MLC fields, collimator wires, a blade, cross-bar, etc., and tumor outlines all at once. It should be appreciated that, by using visual light from the LCD assembly 208 to project the digital images onto the skin of the patient, the simulator machine 200 is allowed to function without a costly mechanical MLC assembly including accessory mounts. It will be appreciated that the term "outlines" is used herein for convenience because the images projected typically are outlines of various structures or shapes. Nevertheless, outlines as used and claimed herein shall be understood as broadly encompassing any type of image.

In one embodiment, the LCD assembly 208 may also project different gray scales to show the different dose levels (e.g., a high dose, a low dose) to be administered during the treatment.

In one embodiment, the quartz halogen light assembly may project visual light on the actual mechanical wires and blades, or digital images of the MLC wires and blades. The visual light may be used to project mechanical shadows onto a mirror and then onto the patient's skin.

At step 440, the outline is temporarily marked on the patient. For example, ink may be used to trace temporary tattoo reference marks of the outline images onto the patient.

At step 445, the patient is transferred to a therapeutic treatment device.

At step 450, during therapeutic treatment, the reference marks on the patient are aligned with field lights on the therapeutic treatment device to properly position the patient. In this way, time is saved in verifying the treatment position of the patient.

Figure 4:
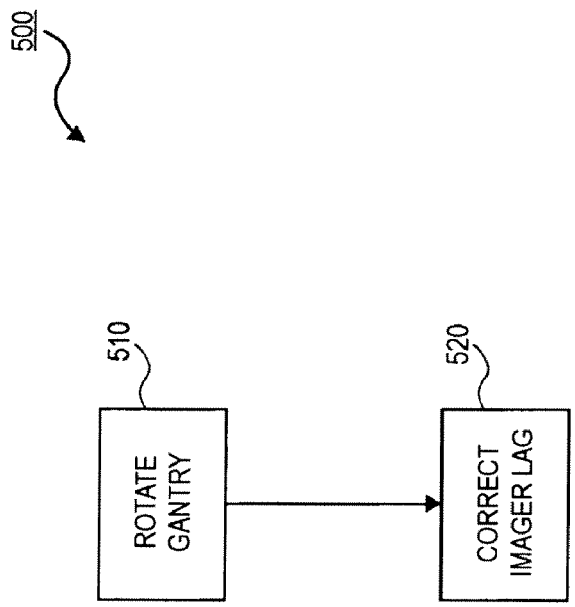
FIG. 4 illustrates one embodiment of a process to correct lag in a flat panel imager during fluoroscopic imaging on the simulator device.

FIG. 4 illustrates one embodiment of correcting lag (e.g. process 500) in a flat panel imager during fluoroscopic imaging on the simulator device. At step 510, the gantry is rotated to a field setup position about the patient while capturing fluoroscopic images of a target volume. At step 520, the lag of a flat panel image is automatically corrected while performing the fluoroscopic images. That is, a correction will be made for any leakage (or lag) of a current generated when the radiation impinges on the imager during fluoroscopic imaging (e.g., 15 to 30 frames per second). By way of example, U.S. provisional patent application Ser. No. 60/419,132 entitled "Method and Apparatus for Non-Linear Background and Lag Correction of Large Area, Flat Panel Image Sensors," filed on Oct. 16, 2002, discloses an exemplary lag correction method, hereby incorporated by reference in its entirety.

Figure 5:
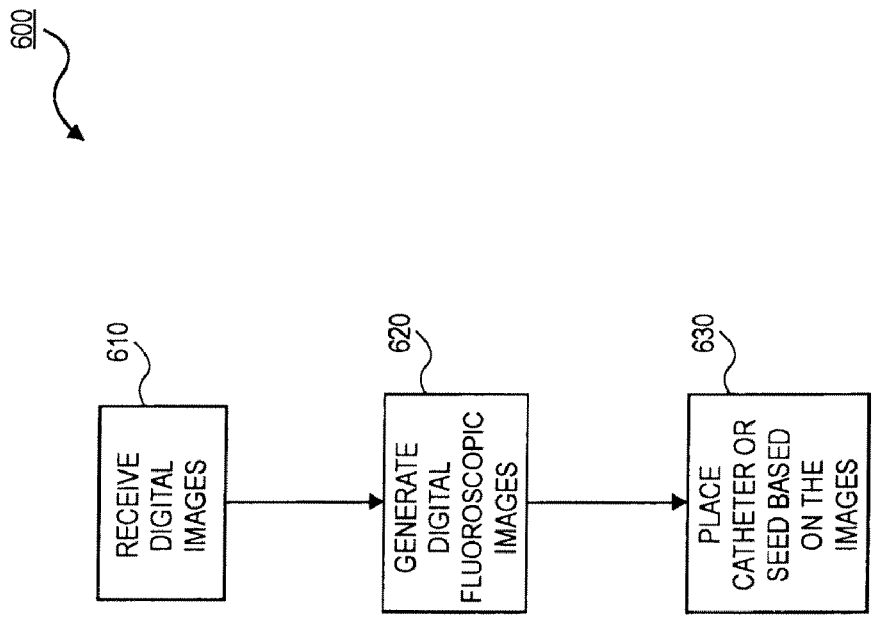
FIG. 5 illustrates one embodiment of a process to perform an image-guided brachytherapy treatment on the simulator device.

FIG. 5 illustrates one embodiment of performing an image-guided brachytherapy treatment on the simulation treatment (e.g. process 600) system 100. At step 610, the simulation treatment system 100 receives digital images of a treatment plan showing the position of a target volume. At step 620, the simulation treatment system 100 generates digital fluoroscopic image(s) of a target volume. At step 630, a care provider ensures the placement of a catheter or seed for brachytherapy based on the images. In one embodiment, a catheter is placed near the target volume based on the images and a radioactive isotope is placed into the catheter to deliver treatment to the target volume. In another embodiment, one or more seeds are placed near the target volume based on the images. In this way, fluoroscopic images are used for visualizing and verifying anatomy during the placement of catheters and seeds, without having to move the patient.

It should be appreciated that the system 100 may perform both brachytherapy planning and imaging. The treatment planning software is integrated into the system 100, allowing easy visualization of the planned placement of the radioactive treatment sources. By being able to display live, undistorted fluoroscopy images, the system 100 makes it much easier for the physician to place the catheters and seeds accurately according to the treatment plan. Variations in placement can be immediately seen and the necessary corrections made to the treatment plan.

In one embodiment, the computer workstation 220 may also control the generator located in a simulator control cabinet located in the drive stand 203. For example, from the workstation 220, a care provider may manually or automatically choose the specific generator settings needed. It should be appreciated that control of the generator is integrated into the workstation 220, controlling the generator settings rather than a separate device, as is typically performed.

The system 100 may also include a collision avoidance system that automatically moves the flat-panel imager 206 away from a potential collision and returns it to the original position once the situation has passed. Thus, protecting patients, operators, and the machine. In one embodiment, the care provider may enter the height and weight of the patient, and then the system will calculate a typical patient size (e.g., head, neck, etc.) to enable closer positioning of the gantry head 204 and imager 206. In an alternative embodiment, the CT image data is used to automatically calculate patient size to enable closer positioning of the imager 206. In yet another alternative embodiment, the dimensions of the treatment machine that will be used to perform the treatment is used to calculate collision avoidance and setup to enable closer positioning of the imager 206. Each embodiment may include hardware and software with both detection and avoidance features, and takes into account accessory mounts and electron applicators.

It should be appreciated that, due to the small size of the imager, the gantry head no longer needs to be capable of moving and can be fixed in a set position in a preferred embodiment. In previous designs, because the imager was a large image intensifier, the gantry head had to be capable of moving to simulate the distance to the patient that could be achieved on the treatment machine. The thinness of the new imager means that these restrictions in treatment setup no longer exist. In embodiments employing a fixed radiation source, the isocenter is more accurately located than in systems with a moveable gantry head.

For example, the fixed gantry head may place the isocenter at, e.g., 100 cm to simulate isocenter distances typical of linear accelerator systems. In order to simulate treatment on therapy systems with a different isocenter distance, such as cobalt machines with an e.g. 80 cm isocenter distance, in a preferred embodiment the software automatically moves the treatment couch 218 20 cm (in the case of an 80 cm isocenter) closer to the gantry head and, as the gantry head is rotated around the patient, the treatment couch 218 is continuously and automatically repositioned to maintain this treatment distance.

It should be appreciated that more or fewer processes may be incorporated into the methods illustrated in FIGS. 2, 3, 4, and 5 without departing from the scope of the invention, and that no particular order is implied by the arrangement of blocks shown and described herein. It further will be appreciated that the method described in conjunction with FIGS. 2, 3, 4, and 5 may be embodied in machine-executable instructions (e.g. software). The instructions can be used to cause a general-purpose or special-purpose processor that is programmed with the instructions to perform the operations described. Alternatively, the operations might be performed by specific hardware components that contain hardwired logic for performing the operations, or by any combination of programmed computer components and custom hardware components. The methods may be provided as a computer program product that may include a machine-readable medium having stored thereon instructions that may be used to program a computer (or other electronic devices) to perform the methods. For the purposes of this specification, the term "machine-readable medium" shall be taken to include any medium that is capable of storing or encoding a sequence of instructions for execution by the machine and that causes the machine to perform any one of the methodologies of the present invention. The term "machine-readable medium" shall accordingly be taken to include, but not be limited to, solid-state memories, optical and magnetic disks, and carrier wave signals. Furthermore, it is common in the art to speak of software, in one form or another (e.g., program, procedure, process, application, module, logic, etc.), as taking an action or causing a result. Such expressions are merely a shorthand way of saying that execution of the software by a computer causes the processor of the computer to perform an action or produce a result.

Thus, a treatment planning, simulation, and verification system has been described. In this way, the simulator machine frees the therapeutic treatment machine to be used exclusively for treatment delivery. It should be appreciated that the simulation system need not include costly components such as an image intensifier tube and a multileaf collimator. The use of a backlit, high-resolution LCD to project multiple digital outlines simultaneously onto the patient provides for a less costly simulator device and a more efficient manner to trace reference marks for the proper positioning and alignment of the patient during treatment.

Furthermore, the cost for film processing and related environmental, health, and safety issues are also overcome. Other issues, such as logistical costs of storing and finding specific patient films when necessary, are also avoided. With a filmless system, these costs are removed and the process of finding patient images throughout a radiotherapy department is made much more efficient. This leads to better access to patient information and, therefore, to better data to support decisions made regarding patient care.

Additional three-dimensional information may be obtained if the system 100 is placed in the proximity of a CT scanner device. In this way, the patient may be situated on the couch 218 during the CT scan, then, upon completion of the CT scan, the couch 218 may be moved from the CT scanner device to the simulator device without moving the patient from the couch 218. In this way, CT imaging and verification imaging is performed in one room, thereby saving time transferring the patient. The couch 218 may rotate at its base to move the patient between devices. Using the same patient positioning system for planning, simulation, and treatment may obtain more accurate setups and significantly reduce setup times and chances of error in treatment. It should also be understood that multiple images from multiple sources might be compared and/or overlaid on the system 100 to perform the method described herein.

Furthermore, in a preferred embodiment, the rotatable gantry 202 is a cast gantry. That is, the rotatable gantry substantially comprises a single cast frame. For example, the rotatable gantry 202 may be an aluminum cast gantry. A cast gantry provides increased structural integrity than would otherwise be available from a non-cast gantry.

While the invention has been described in terms of several embodiments, those skilled in the art will recognize that the invention is not limited to the embodiments described. The method and apparatus of the invention can be practiced with modification and alteration within the scope of the appended claims. The description is thus to be regarded as illustrative instead of limiting on the invention.

What is claimed is:

1. A single treatment simulator system comprising:
   a treatment planning component to receive a treatment plan;
   a simulation component to simulate an execution of the treatment plan on a patient;
   a third component to adjust the treatment plan based on the simulated execution of the treatment plan; and
   a fourth component to save an adjustment to the treatment plan;
   wherein the single treatment simulator system comprises the treatment planning component, the simulation component, the third component, and the fourth component,
   wherein the treatment plan includes a digitally reconstructed radiograph image,
   wherein the simulation component generates digital fluoroscopy images of a target volume to confirm the digitally reconstructed radiograph image, and wherein adjusting comprises:
   adjusting automatically at the single treatment simulator system the treatment plan based on movement in a video display of a digital fluoroscopy image.

2. The system of claim 1, wherein adjusting includes adjusting treatment field information to allow for movement in a field.

3. The system of claim 1, wherein adjusting includes adjusting gating information in the treatment plan.

4. The system of claim 1 wherein the movement in the video display of the digital fluoroscopic image comprises movement of a patient's internal anatomy in a digital video signal from a real time digital x-ray imager.

5. The system of claim 1 wherein the digital fluoroscopic image comprises a digital video signal from a real time digital x-ray imager.

6. A single treatment simulator system comprising:
   a treatment planning component to receive a treatment plan;
   a simulation component to simulate an execution of the treatment plan on a patient;
   a third component to adjust the treatment plan based on the simulated execution of the treatment plan; and
   a fourth component to save an adjustment to the treatment plan;
   wherein the single treatment simulator system comprises the treatment planning component, the simulation component, the third component, and the fourth component, and wherein adjusting comprises:
   displaying at the single treatment simulator system a digital image of a patient, wherein the digital image is generated on the single treatment simulator system;
   providing at the single treatment simulator system, an input associated with the digital image;
   automatically adjusting at the single treatment simulator system, the treatment plan based on the input associated with the digital image; and
   recalculating at the single treatment simulator system a treatment plan based on the input associated with the digital image.

7. The system of claim 6, wherein displaying the digital image includes overlaying a simulator digital image and a digitally reconstructed radiograph image.

8. The system of claim 7, further comprising:
automatically displaying fields of data based on the digital image.

9. The system of claim 6, wherein the providing includes providing a radiation field input.

10. A method of performing brachytherapy comprising:
placing a patient on a patient support;
producing an image of the patient using a flat panel imager while the patient is on the patient support;
adjusting a treatment plan for placement of a radiation source in the patient based at least in part on the image while the patient is on the patient support; and then treating the patient according to the treatment plan while the patient is on the patient support, wherein adjusting comprises:
adjusting automatically at a single treatment system the treatment plan based on movement in a video display of a digital fluoroscopy image.

11. The method of claim 10, wherein adjusting includes adjusting treatment field information to allow for movement of the patient in a field.

12. The method of claim 10, wherein adjusting includes adjusting gating information in the treatment plan.

* * * * *